(12) United States Patent
Halverson

(10) Patent No.: US 8,535,945 B2
(45) Date of Patent: Sep. 17, 2013

(54) SYSTEM AND METHOD FOR CONCENTRATING SAMPLES

(75) Inventor: Kurt J. Halverson, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 169 days.

(21) Appl. No.: 13/131,641

(22) PCT Filed: Nov. 30, 2009

(86) PCT No.: PCT/US2009/066038
§ 371 (c)(1),
(2), (4) Date: May 27, 2011

(87) PCT Pub. No.: WO2010/080232
PCT Pub. Date: Jul. 15, 2010

(65) Prior Publication Data
US 2011/0250586 A1    Oct. 13, 2011

Related U.S. Application Data

(60) Provisional application No. 61/139,144, filed on Dec. 19, 2008.

(51) Int. Cl.
| | | |
|---|---|---|
| *G01N 35/00* | (2006.01) | |
| *B04B 1/00* | (2006.01) | |
| *B01L 3/14* | (2006.01) | |
| *G01N 1/40* | (2006.01) | |
| *C12Q 1/14* | (2006.01) | |
| *B01D 33/00* | (2006.01) | |

(52) U.S. Cl.
CPC .................................. *G01N 1/4077* (2013.01)
USPC ............. 436/45; 210/324; 210/650; 210/436; 422/533; 422/548; 422/616; 435/34

(58) Field of Classification Search
USPC ........................................................ 436/45
See application file for complete search history.

(56) References Cited

U.S. PATENT DOCUMENTS 4,539,256 A    9/1985   Shipman
4,632,761 A *  12/1986  Bowers et al. ............... 210/650
(Continued)

FOREIGN PATENT DOCUMENTS

EP   0370238   5/1990
FR   2625691   7/1989
(Continued)

OTHER PUBLICATIONS

International Search Report PCT/2009/066038 Mar. 31, 2010, 4 pgs.
(Continued)

*Primary Examiner* — Jill Warden
*Assistant Examiner* — Julie Tavares
(74) *Attorney, Agent, or Firm* — Nicole J. Einerson

(57) ABSTRACT

A system and method for concentrating samples. The system can include a first container adapted to contain a sample. The first container can include a first portion and a second portion adapted to be removably coupled to the first portion. The system can further include a second container comprising the second portion and a third portion adapted to be removably coupled to the second portion. The method can include centrifuging the first container in a first orientation toward the second portion of the first container; retaining a concentrate of the sample in the second portion of the first container; and centrifuging the second container in a second orientation toward the third portion of the second container, such that the concentrate retained in the second portion is moved into the third portion of the second container, the second orientation being different from the first orientation.

15 Claims, 4 Drawing Sheets

(56) References Cited

U.S. PATENT DOCUMENTS

| | | | |
|---|---|---|---|
| 4,698,311 A | 10/1987 | Hall | |
| 4,726,989 A | 2/1988 | Mrozinski | |
| 4,867,881 A | 9/1989 | Kinzer | |
| 4,956,298 A | 9/1990 | Diekmann | |
| 4,959,301 A | 9/1990 | Weaver | |
| 5,120,594 A | 6/1992 | Mrozinski | |
| 5,234,667 A | 8/1993 | Radtke | |
| 5,260,360 A | 11/1993 | Mrozinski | |
| 5,620,662 A | 4/1997 | Perlman | |
| 5,716,798 A | 2/1998 | Monthony | |
| 5,770,440 A | 6/1998 | Berndt | |
| 5,820,767 A | 10/1998 | Kane | |
| 5,824,272 A | 10/1998 | Uchida | |
| 5,833,860 A | 11/1998 | Kopaciewicz | |
| 5,888,594 A | 3/1999 | David | |
| 6,143,247 A | 11/2000 | Sheppard, Jr. | |
| 6,197,579 B1 | 3/2001 | Van Vlasselaer | |
| 6,221,655 B1 * | 4/2001 | Fung et al. | 435/288.1 |
| 6,386,699 B1 | 5/2002 | Ylitalo | |
| 6,391,578 B2 | 5/2002 | Williams | |
| 6,420,622 B1 | 7/2002 | Johnston | |
| 6,458,553 B1 | 10/2002 | Colin | |
| 6,566,508 B2 | 5/2003 | Bentsen | |
| 6,617,002 B2 | 9/2003 | Wood | |
| 6,627,159 B1 | 9/2003 | Bedingham | |
| 6,696,286 B1 | 2/2004 | Halverson | |
| 6,720,187 B2 | 4/2004 | Bedingham | |
| 6,730,397 B2 | 5/2004 | Melancon | |
| 6,734,401 B2 | 5/2004 | Bedingham | |
| 6,814,935 B2 | 11/2004 | Harms | |
| 6,867,342 B2 | 3/2005 | Johnston | |
| 6,869,666 B2 | 3/2005 | Deeb | |
| 6,987,253 B2 | 1/2006 | Bedingham | |
| 7,026,168 B2 | 4/2006 | Bedingham | |
| 7,164,107 B2 | 1/2007 | Bedingham | |
| 7,223,364 B1 | 5/2007 | Johnston | |
| 7,435,933 B2 | 10/2008 | Bedingham | |
| 7,445,752 B2 | 11/2008 | Harms | |
| 2002/0128578 A1 | 9/2002 | Johnston | |
| 2003/0036054 A1 | 2/2003 | Ladisch | |
| 2003/0235677 A1 | 12/2003 | Hanschen | |
| 2004/0038425 A1 | 2/2004 | Ferguson | |
| 2004/0058408 A1 | 3/2004 | Thomas | |
| 2004/0132208 A1 | 7/2004 | Burshteyn | |
| 2004/0179974 A1 | 9/2004 | Bedingham | |
| 2006/0188396 A1 | 8/2006 | Bedingham | |
| 2006/0189000 A1 | 8/2006 | Bedingham | |
| 2006/0228811 A1 | 10/2006 | Bedingham | |
| 2006/0269451 A1 | 11/2006 | Bedingham | |
| 2007/0003441 A1 | 1/2007 | Wohleb | |
| 2007/0134784 A1 | 6/2007 | Halverson | |
| 2007/0151924 A1 | 7/2007 | Mir | |
| 2007/0196884 A1 | 8/2007 | Bodini | |
| 2011/0039220 A1 | 2/2011 | Zhou | |

FOREIGN PATENT DOCUMENTS

| | | |
|---|---|---|
| JP | 2005-238158 | 9/2005 |
| WO | WO 00/57178 | 9/2000 |
| WO | WO 01/87486 | 11/2001 |
| WO | WO 02/00347 | 1/2002 |
| WO | WO 02/01180 | 1/2002 |
| WO | WO 02/01181 | 1/2002 |
| WO | WO 02/086454 | 10/2002 |
| WO | WO 02/090091 | 11/2002 |
| WO | WO 2004/000569 | 12/2003 |
| WO | WO 2004/013604 | 2/2004 |
| WO | WO 2004/058405 | 7/2004 |
| WO | WO 2005/108950 | 11/2005 |
| WO | WO 2007/070310 | 6/2007 |
| WO | WO 2007/137257 | 11/2007 |
| WO | WO 2010/071764 | 6/2010 |
| WO | WO 2010/078234 | 7/2010 |
| WO | WO 2010/080232 | 7/2010 |
| WO | WO 2010/080236 | 7/2010 |
| WO | WO 2011/063332 | 5/2011 |
| WO | WO 2011/152967 | 12/2011 |
| WO | WO 2011/153085 | 12/2011 |
| WO | WO 2011/156251 | 12/2011 |
| WO | WO 2011/156258 | 12/2011 |

OTHER PUBLICATIONS

Stettler et al. "New Disposable Tubes for Rapid and Precise Biomass Assessment for Suspension Cultures of Mammalian Cells". Biotechnology and Bioengineering 95:6, Dec. 20, 2006, pp. 1228-1233.

Standard Methods for the Examination of Water and Wastewater; Membrane Filter Technique for Members of the Coliform. American Public Health Association, American Water Works Association, Water Environment Federation. Washington DC (1999), 8 pages.

"Fast, reproducible and reliable determination of biomass in suspension cell cultures with VoluPAC tubes", Nature Methods Oct. 3, 2006, [retrieved from the internet on Oct. 20, 2008] URL www.nature.com/app_notes/nmeth/2006/061710/full/nmeth942.html, 7 pages.

Ingham et al., "The micro-Petri dish, a million-well growth chip for the culture and high throughput screening of microorganisms", PNAS, Nov. 2007, vol. 104, No. 46, 18217-18222.

Chilvers et al., "Synthesis and evaluation of novel fluorogenic substrates for the detection of bacterial β-galactosidase", Journal of Applied Microbiology,(2001), 91, 1118-1130.

* cited by examiner

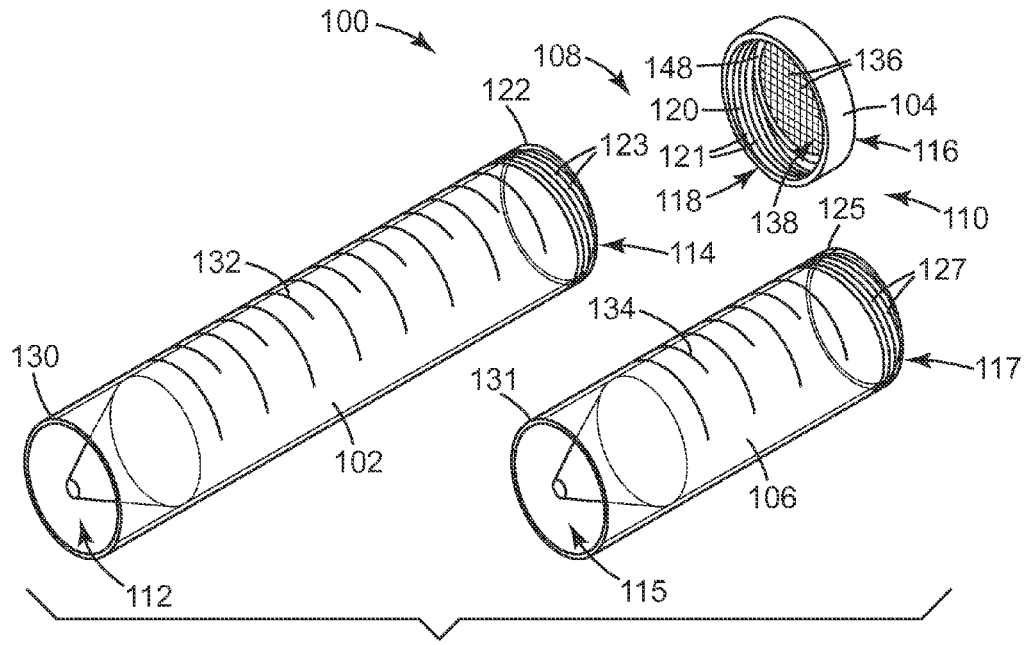
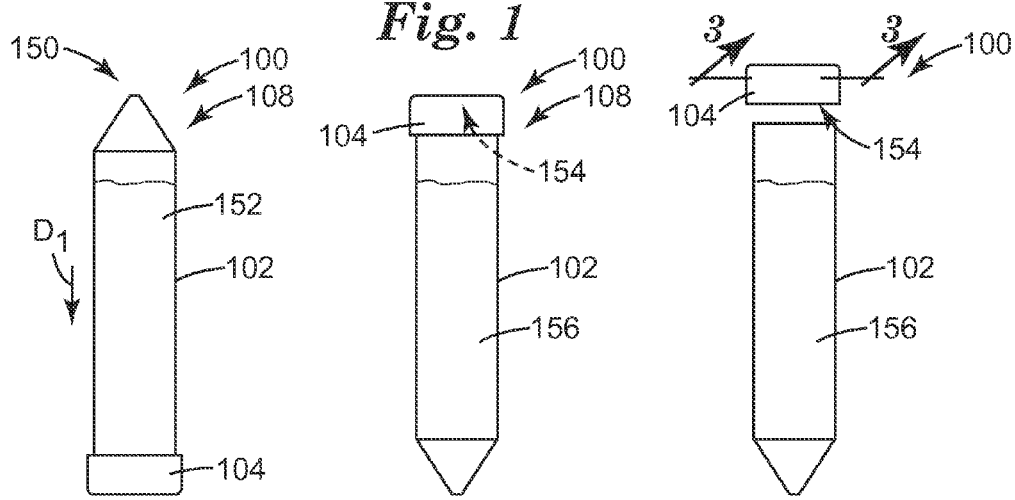
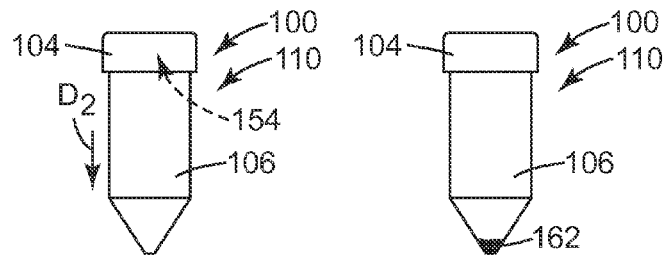
Fig. 1
Fig. 2A    Fig. 2B    Fig. 2C
Fig. 2D    Fig. 2E

SYSTEM AND METHOD FOR CONCENTRATING SAMPLES

CROSS REFERENCE TO RELATED APPLICATIONS

This is a national stage filing under 35 U.S.C. 371 of PCT/US2009/066038, filed Nov. 30, 2009, which claims priority to U.S. Provisional Application Ser. No. 61/139,144, filed Dec. 19, 2008, the disclosure of which is incorporated by reference in its entirety herein.

FIELD

The present disclosure generally relates to a system and method for concentrating samples for sample testing, and particularly, for concentrating liquid samples.

BACKGROUND

Testing aqueous samples for the presence of microorganisms (e.g., bacteria, viruses, fungi, spores, etc.) and/or other analytes of interest (e.g., toxins, allergens, hormones, etc.) can be important in a variety of applications, including food and water safety, infectious disease diagnostics, and environmental surveillance. For example, comestible samples, such as foods, beverages, and/or public water consumed by the general population may contain or acquire microorganisms or other analytes, which can flourish or grow as a function of the environment in which they are located. This growth may lead to the proliferation of pathogenic organisms, which may produce toxins or multiply to infective doses. By way of further example, a variety of analytical methods can be performed on samples of non-comestible samples (e.g., groundwater, urine, etc.) to determine if a sample contains a particular analyte. For example, groundwater can be tested for a microorganism or a chemical toxin; and urine can be tested for a variety of diagnostic indicators to enable a diagnosis (e.g., diabetes, pregnancy, etc.).

SUMMARY

One aspect of the present disclosure provides a method for concentrating a sample. The method can include providing a first container adapted to contain a sample. The first container can include a first portion and a second portion adapted to be removably coupled to the first portion. The second portion can include a microstructured surface. The method can further include centrifuging the first container in a first orientation toward the second portion of the first container; retaining a concentrate of the sample in the microstructured surface of the second portion of the first container; removing the second portion of the first container from the first portion; coupling the second portion to a third portion to form a second container; and centrifuging the second container in a second orientation toward the third portion of the second container, such that the concentrate retained in the microstructured surface of the second portion is moved into the third portion of the second container, the second orientation being different from the first orientation.

Another aspect of the present disclosure provides a method for concentrating a sample. The method can include providing a first container adapted to contain a sample. The first container can include a first portion and a second portion adapted to be removably coupled to the first portion. The method can further include centrifuging the first container in a first orientation toward the second portion of the first container; retaining a concentrate of the sample in the second portion of the first container; removing the second portion of the first container from the first portion; coupling the second portion to a third portion to form a second container; and centrifuging the second container in a second orientation toward the third portion of the second container, such that the concentrate retained in the second portion is moved into the third portion of the second container, the second orientation being different from the first orientation.

Another aspect of the present disclosure provides a system for concentrating a sample. The system can include a first container adapted to contain a sample. The first container can include a first portion and a second portion adapted to be removably coupled to the first portion. The second portion can include a microstructured surface adapted to receive a concentrate of the sample when the first container is exposed to a first centrifugal force. The microstructured surface of the second portion can be further adapted to retain at least a portion of the concentrate of the sample under normal gravitational forces. The system can further include a second container comprising the second portion and a third portion adapted to be removably coupled to the second portion. The third portion can be adapted to receive the concentrate from the second portion when the second container is exposed to a second centrifugal force.

Another aspect of the present disclosure provides a system for concentrating a sample. The system can include a first container adapted to contain a sample. The first container can include a first portion and a second portion adapted to be removably coupled to the first portion. The second portion can be adapted to receive a concentrate of the sample when the first container is exposed to a first centrifugal force. The second portion can be further adapted to retain at least a portion of the concentrate of the sample under normal gravitational forces. The system can further include a second container comprising the second portion and a third portion adapted to be removably coupled to the second portion. The third portion can be adapted to receive the concentrate from the second portion when the second container is exposed to a second centrifugal force.

Other features and aspects of the present disclosure will become apparent by consideration of the detailed description and accompanying drawings.

BRIEF DESCRIPTION OF THE DRAWINGS

FIG. 1 is a perspective view of a sample concentration system according to one embodiment of the present disclosure, the sample concentration system including a first portion, a second portion, and a third portion.

FIGS. 2A-2E are side elevational views of the sample concentration system of FIG. 1 and illustrate a sample concentration method according to one embodiment of the present disclosure.

DETAILED DESCRIPTION

Figure 3:
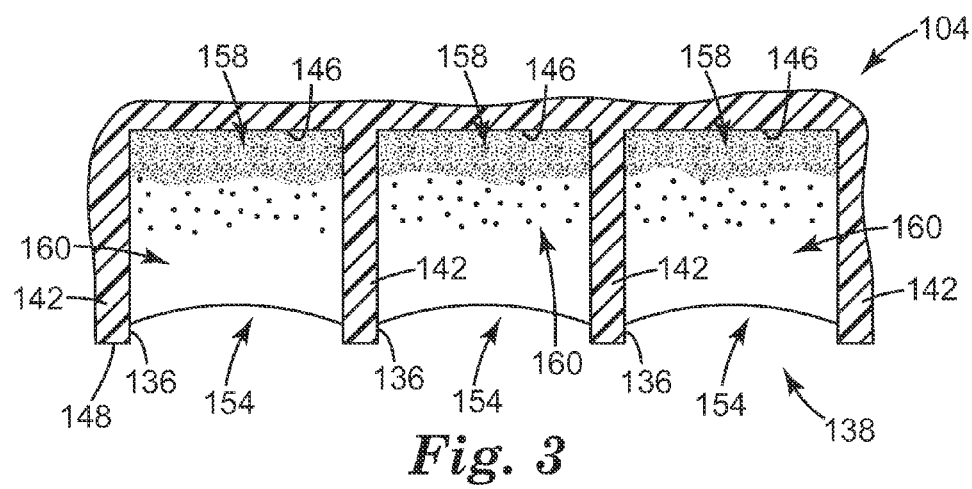
FIG. 3 is an enlarged schematic partial cross-sectional view of the second portion of the sample concentration system of FIGS. 1 and 2A-2E at a point in time, taken along line 3-3 in FIG. 2C.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompasses both direct and indirect couplings. It is to be understood that other embodiments may be utilized, and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

In a variety of samples that are desired to be tested for an analyte of interest, the analyte can be present in the sample at a low concentration, which can require that the sample be concentrated into a smaller volume in order to reach an appropriate concentration of an analyte of interest so as to achieve a detection threshold of an analytical technique. In some existing systems and methods, centrifugation is used for samples having a high enough analyte concentration (e.g., bacterial concentration) to form a visible, packed "pellet" in the base of the centrifugation flask.

The supernatant resulting from the centrifugation process can then be removed by decanting or aspiration. Visual inspection can be used in both decanting and aspiration to determine the appropriate volume of supernatant to be removed, and significant analyte loss can occur at the interface between the supernatant and the pellet. In addition, in samples having a particularly low concentration of the analyte of interest, the analyte may migrate to the base of the centrifugation flask during centrifugation but does not form a visible pellet and is not tightly packed. In such situations, the analyte can be easily dislodged during decanting or aspiration, which can decrease the overall collection efficiency of the analyte of interest, and can reduce the accuracy of the sample testing procedure.

As a result, in some existing systems and methods, filtration is employed to concentrate low-concentration samples. While filtration can increase the concentration of the analyte of interest in the sample, retrieving the concentrated sample from the filter can be difficult and/or time-consuming. For example, in some situations, large elution volumes can be required to backflush or wash the concentrated sample off of the filter, particularly for large initial sample volumes that may have required a filter having a large diameter. In addition, portions of the sample can become irreversibly trapped in the filter during filtration. Trapping can be overcome using isoporous filters, however, filtration through isoporous filters can be slow, and the pores of the isoporous filter can easily and rapidly plug during filtration.

The present disclosure generally relates to a system and method for concentrating samples, and particularly, for concentrating liquid samples, and more particularly, for concentrating dilute aqueous samples, for example, to improve collection efficiency and/or sample testing accuracy.

Such samples to be concentrated can be obtained in a variety of ways. For example, in some embodiments, the sample to be concentrated itself is a liquid sample, such as a dilute liquid sample and/or a dilute aqueous sample. In some embodiments, the sample can include the liquid resulting from washing or rinsing a source of interest (e.g., a surface, fomite, etc.) with a diluent. In some embodiments, the sample can include the filtrate resulting from filtering or settling a liquid composition resulting from combining a source of interest with an appropriate diluent. That is, large insoluble matter and/or matter having a lower or higher density than the analyte(s) of interest, such as various foods, fomites, or the like, can be removed from a liquid composition in a first filtration or settling step to form the sample that will be concentrated using a sample concentration system and method of the present disclosure.

The term "source" can be used to refer to a food or nonfood desired to be tested for analytes. The source can be a solid, a liquid, a semi-solid, a gelatinous material, and combinations thereof. In some embodiments, the source can be provided by a substrate that was used, for example, to collect the source from a surface of interest. In some embodiments, the liquid composition can include the substrate, which can be further broken apart (e.g., during an agitation or dissolution process) to enhance retrieval of the source and any analyte of interest. The surface of interest can include at least a portion of a variety of surfaces, including, but not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used to obtain a sample that is to be concentrated using the sample concentration system and method of the present disclosure.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, wood, soil, sediment, medicines, cosmetics, dietary supplements (e.g., ginseng capsules), pharmaceuticals, fomites, other suitable non-comestible materials, and combinations thereof.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "analyte" is generally used to refer to a substance to be detected (e.g., by a laboratory or field test). A sample can be tested for the presence, quantity and/or viability of particular analytes. Such analytes can be present within a source (e.g., on the interior), or on the exterior (e.g., on the outer surface) of a source. Examples of analytes can include, but are not limited to, microorganisms, biomolecules, chemicals (e.g. pesticides, antibiotics), metal ions (e.g. mercury ions, heavy metal ions), metal-ion-containing complexes (e.g., complexes comprising metal ions and organic ligands), and combinations thereof.

A variety of testing methods can be used to identify, quantitate, and/or elucidate the viability of an analyte, including, but not limited to, microbiological assays, biochemical assays (e.g. immunoassay), or a combination thereof. Specific examples of testing methods that can be used include, but are not limited to, lateral flow assays, titration, thermal analysis, microscopy (e.g., light microscopy, fluorescent microscopy, immunofluorescent microscopy, scanning electron microscopy (SEM), transmission electron microscopy (TEM)), spectroscopy (e.g., mass spectroscopy, nuclear magnetic resonance (NMR) spectroscopy, Raman spectroscopy, infrared (IR) spectroscopy, x-ray spectroscopy, attenuated total reflectance spectroscopy, Fourier transform spectroscopy, gamma-ray spectroscopy, etc.), spectrophotometry (e.g., absorbance, fluorescence, luminescence, etc.), chromatography (e.g., gas chromatography, liquid chromatography, ion-exchange chromatography, affinity chromatography, etc.), electrochemical analysis, genetic techniques (e.g., polymerase chain reaction (PCR), transcription mediated amplification (TMA), hybridization protection assay (HPA), DNA or RNA molecular recognition assays, etc.), adenosine triphosphate (ATP) detection assays, immunological assays (e.g., enzyme-linked immunosorbent assay (ELISA)), cytotoxicity assays, viral plaque assays, techniques for evaluating cytopathic effect, culture techniques such as those that can be done using a growth medium (e.g., agar) and/or 3M™ PETRIFILM™ plates (e.g., and imaged, quantified and/or interpreted using a 3M™ PETRIFILM™ plate reader (3M Company, St. Paul, Minn.)), other suitable analyte testing methods, or a combination thereof.

The term "microorganism" is generally used to refer to any prokaryotic or eukaryotic microscopic organism, including without limitation, one or more of bacteria (e.g., motile or vegetative, Gram positive or Gram negative), viruses (e.g., Norovirus, Norwalk virus, Rotavirus, Adenovirus, DNA viruses, RNA viruses, enveloped, non-enveloped, human immunodeficiency virus (HIV), human Papillomavirus (HPV), etc.), bacterial spores or endospores, algae, fungi (e.g., yeast, filamentous fungi, fungal spores), prions, mycoplasmas, and protozoa. In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacterium* spp. Particular examples of pathogens can include, but are not limited to, *Escherichia coli* including enterohemorrhagic *E. coli* e.g., serotype O157:H7, O129:H11; *Pseudomonas aeruginosa*; *Bacillus cereus*; *Bacillus anthracis*; *Salmonella enteritidis*; *Salmonella enterica* serotype Typhimurium; *Listeria monocytogenes*; *Clostridium botulinum*; *Clostridium perfringens*; *Staphylococcus aureus*; methicillin-resistant *Staphylococcus aureus*; *Campylobacter jejuni*; *Yersinia enterocolitica*; *Vibrio vulnificus*; *Clostridium difficile*; vancomycin-resistant *Enterococcus*; and *Enterobacter [Cronobacter] sakazakii*. Environmental factors that may affect the growth of a microorganism can include the presence or absence of nutrients, pH, moisture content, oxidation-reduction potential, antimicrobial compounds, temperature, atmospheric gas composition and biological structures or barriers.

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, a protein, a polynucleotide, a lipid, a phospholipid, a saccharide, a polysaccharide, and combinations thereof. Specific examples of biomolecules can include, but are not limited to, a metabolite (e.g., staphylococcal enterotoxin), an allergen (e.g., peanut allergen(s), egg allergen(s), pollens, dust mites, molds, danders, or proteins inherent therein, etc.), a hormone, a toxin (e.g., *Bacillus* diarrheal toxin, aflatoxin, *Clostridium difficile* toxin etc.), RNA (e.g., mRNA, total RNA, tRNA, etc.), DNA (e.g., plasmid DNA, plant DNA, etc.), a tagged protein, an antibody, an antigen, ATP, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source can include soluble matter and insoluble matter (e.g., cell debris). Insoluble matter is sometimes referred to as particulate(s) or debris and can include portions of the source material itself (i.e., from internal portions or external portions (e.g., the outer surface) of the source) or other source residue or debris resulting from an agitation process. In addition, a liquid composition comprising the source and a diluent can include more dense matter (i.e., matter having a higher density than the diluent and other matter in the mixture) and less dense matter (i.e., matter having a lower density than the diluent and other matter in the mixture). As a result, a diluent of the sample can be selected, such that the analyte(s) of interest is(are) more dense than the diluent and can be concentrated via settling (e.g., centrifugation).

The term "diluent" is generally used to refer to a liquid added to a source material to disperse, dissolve, suspend, emulsify, wash and/or rinse the source. A diluent can be used in forming a liquid composition, from which a sample to be concentrated using the sample concentration system and method of the present disclosure can be obtained. In some embodiments, the diluent is a sterile liquid. In some embodiments, the diluent can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); enrichment or growth medium comprising nutrients (e.g., that promote selective growth of desired microorganism(s)) and/or growth inhibitors (e.g., that inhibit the growth of undesired microorganism(s)); pH buffering agents; enzymes; indicator molecules (e.g. pH or oxidation/reduction indicators); spore germinants; an agent to neutralize sanitizers (e.g., sodium thiosulfate neutralization of chlorine); an agent intended to promote bacterial resuscitation (e.g., sodium pyruvate); stabilizing agents (e.g., that stabilize the analyte(s) of interest, including solutes, such as sodium chloride, sucrose, etc.); or a combination thereof. In some embodiments, the diluent can include sterile water (e.g., sterile double-distilled water (ddH$_2$O)); one or more organic solvents to selectively dissolve, disperse, suspend, or emulsify the source; aqueous organic solvents, or a combination thereof. In some embodiments, the diluent is a sterile buffered solution (e.g., Butterfield's Buffer, available from Edge Biological, Memphis Tenn.). In some embodiments, the diluent is a selective or semi-selective nutrient formulation, such that the diluent may be used in the selective or semi-selective growth of the desired analyte(s) (e.g., bacteria). In such embodiments, the diluent can be incubated with a source for a period of time (e.g., at a specific temperature) to promote such growth and/or development of the desired analyte(s).

Examples of growth medium can include, but are not limited to, Tryptic Soy Broth (TSB), Buffered Peptone Water (BPW), Universal Pre-enrichment Broth (UPB), Listeria Enrichment Broth (LEB), Lactose Broth, Bolton broth, or other general, non-selective, or mildly selective media known to those of ordinary skill in the art. The growth medium can include nutrients that support the growth of more than one desired microorganism (i.e., analyte of interest).

Examples of growth inhibitors can include, but are not limited to, bile salts, sodium deoxycholate, sodium selenite, sodium thiosulfate, sodium nitrate, lithium chloride, potassium tellurite, sodium tetrathionate, sodium sulphacetamide, mandelic acid, selenite cysteine tetrathionate, sulphamethazine, brilliant green, malachite green oxalate, crystal violet, Tergitol 4, sulphadiazine, amikacin, aztreonam, naladixic acid, acriflavine, polymyxin B, novobiocin, alafosfalin, organic and mineral acids, bacteriophages, dichloran rose bengal, chloramphenicol, chlortetracycline, certain concentrations of sodium chloride, sucrose and other solutes, and combinations thereof.

The term "filtering" is generally used to refer to the process of separating matter by size, charge and/or function. For example, filtering can include separating soluble matter and a solvent (e.g., diluent) from insoluble matter, or filtering can include separating soluble matter, a solvent and relatively small insoluble matter from relatively large insoluble matter. As a result, a liquid composition can be "pre-filtered" to obtain a sample that is to be concentrated using the sample concentration systems and methods of the present disclosure. A variety of filtration methods can be used, including, but not limited to, passing the liquid composition (e.g., comprising a source of interest, from which a sample to concentrated can be obtained) through a filter, other suitable filtration methods, and combinations thereof.

"Settling" is generally used to refer to the process of separating matter by density, for example, by allowing the more dense matter in the liquid composition (i.e., the matter having a higher density than the diluent and other matter in the mixture) to settle or sink and/or by allowing the less dense matter in the liquid composition (i.e., the matter having a lower density than the diluent and other matter in the mixture) to rise or float. Settling may occur by gravity or by centrifugation. The more dense matter can then be separated from the less dense matter (and diluent) by aspirating the less dense (i.e., unsettled or floating) and diluent from the more dense matter, decanting the less dense matter and diluent, or a combination thereof. Pre-settling steps can be used in addition to or in lieu of pre-filtering steps to obtain a sample that is to be concentrated using the sample concentration systems and methods of the present disclosure.

A "filter" is generally used to describe a device used to separate the soluble matter (or soluble matter and relatively small insoluble matter) and solvent from the insoluble matter (or relatively large insoluble matter) in a liquid composition and/or to filter a sample during sample concentration. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or non-uniform process, which can be calendered), a surface filter, a depth filter, a membrane (e.g., a ceramic membrane (e.g., ceramic aluminum oxide membrane filters available under the trade designation ANOPORE from Whatman Inc., Florham Park, N.J.), a polycarbonate membrane (e.g., track-etched polycarbonate membrane filters available under the trade designation NUCLEOPORE from Whatman, Inc.)), a polyester membrane (e.g., comprising track-etched polyester, etc.), a sieve, glass wool, a frit, filter paper, foam, etc., and combinations thereof.

In some embodiments, the term "filtrate" is generally used to describe the liquid remaining after the insoluble matter (or at least the relatively large insoluble matter) has been separated or removed from a liquid composition. In some embodiments, the term "supernatant" is generally used to describe the liquid remaining after the more dense matter has been separated or removed from a liquid composition. Such a filtrate and/or supernatant can form a sample to be concentrated by the sample concentration systems and methods of the present disclosure.

The term "microstructure" or "microstructured feature," and derivatives thereof, is generally used to refer to a structure or a feature having a structure that is a recognizable geometric shape that either protrudes (e.g., a wall) or is depressed (e.g., a well defined at least partially by the wall). For example, a microstructure can include a microstructured well formed to retain a liquid, a solid, a semi-solid, a gelatinous material, another suitable material, or a combination thereof. A microstructure can also include a wall or a base that at least partially defines a microstructured well. Furthermore, a microstructure can include a protrusion, a recess, or the like that is present on any of the above-described microstructures. For example, a microstructured well or wall can be textured, and such textures can also be referred to as microstructures.

The term "microstructured surface" is generally used to refer to a surface that comprises microstructures or microstructured features.

The term "microreplicate" and derivatives thereof, is generally used to refer to the production of a microstructured surface through a process where the structured surface features retain an individual feature fidelity during and after manufacture.

The term "primary," when used with reference to a microstructure, is generally used to refer to a microstructure having the largest scale of any microstructure on the same surface.

The term "secondary," when used with reference to a microstructure, is generally used to refer to a microstructure having a smaller scale microstructure relative to one or more primary microstructures on the same surface.

FIG. 1 illustrates a sample concentration system 100 according to one embodiment of the present disclosure. The sample concentration system 100 includes a first portion 102, a second portion 104, and a third portion 106. In some embodiments, the first portion 102 and the second portion 104 can be removably coupled together to form a first container 108. In some embodiments, the first portion 102 and the third portion 106 can be removably coupled together to form a second container 110.

In general, a sample concentration method can be performed using the sample concentration system 100 of FIG. 1 as follows: a sample can be placed in the first portion 102, and the first portion 102 can be coupled to the second portion 104 to form the first container 108. The first container 108 can be centrifuged toward the second portion 104 to form a concentrate of the sample in the second portion 104 that is retained in the second portion 104. The second portion 104 can be removed from the first portion 102 and coupled to the third portion 106 to form the second container 110, and the second container 110 can be centrifuged away from the second portion 104 to move the concentrate of the sample into the third portion 106. A sample concentration method of the present disclosure will be described in greater detail below with reference to FIGS. 2A-2E.

For the sake of simplicity, the first container 108 will be described as including the first portion 102 and the second portion 104, and the second container 110 will be described as including the second portion 104 and the third portion 106. However, it should be understood that some embodiments of the sample concentration system 100 do not include the third portion 106, and in such embodiments, the first portion 102 can be used in the second container 110 as well as the first container 108. For example, the first portion 102 can be cleaned and reused in the second container 110.

The first container 108 is adapted to contain a sample that is to be concentrated, for example, for further processing, such as testing for one or more analytes of interest. The sample is generally a liquid sample, in some embodiments, is a dilute liquid sample (i.e., any analyte of interest present in the sample is present at a low concentration), and in some embodiments, is a dilute aqueous sample. The first container 108 can be sized and shaped, as desired, to accommodate the sample to be concentrated, and the shape and configuration of the first portion 102 and the second portion 104 is shown by way of example only.

As described above, the first portion 102 and the second portion 104 can be removably coupled together to form the first container 108. By way of example only, the first portion 102 is illustrated in FIG. 1 as being an elongated tube having a closed end 112 and an open end 114, and the second portion 104 is illustrated as being a cap having a closed end 116 and an open end 118. The open end 118 of the second portion 104 is dimensioned to receive at least a portion of the first portion 102, and particularly, the open end 114 of the first portion 102, such that coupling the second portion 104 and the first portion 102 together closes and/or covers the open end 114 of the first portion 102. By way of further example, the second portion 104 includes an inner surface 120 that includes one or more threads 121, and the first portion 102 includes an outer surface 122 that includes one or more threads 123 adjacent the open end 114. The threads 121 of the second portion 104 are configured to cooperate and engage with the threads 123 of the first portion 102, such that the second portion 104 and the first portion 102 can be coupled together. In some embodiments, the first portion 102 and the second portion 104 can be coupled together to form a first container 108 that is sealed from ambience (e.g., such that the first container 108 includes a liquid-tight seal, a hermetic seal, or a combination thereof). For example, in some embodiments, one or both of the first portion 102 and the second portion 104 can include one or more seals (e.g., o-rings).

By way of example only, the first portion 102 includes a tapered closed end 112. By way of further example, the first portion 102 includes a flange 130 which extends from a sidewall of the first portion 102 to the same distance as the terminus of the tapered closed end 112. The flange 130 can allow the first portion 102 to be stood on end to facilitate handling, storage and/or transportation of the first portion 102.

As described above, the second portion 104 and the third portion 106 can be removably coupled together to form the second container 110. By way of example only, the third portion 106 is illustrated in FIG. 1 as being an elongated tube having a closed end 115 and an open end 117. The open end 118 of the second portion 104 is dimensioned to receive at least a portion of the third portion 106, and particularly, the open end 117 of the third portion 106, such that coupling the second portion 104 and the third portion 106 together closes and/or covers the open end 117 of the third portion 106. By way of further example, the third portion 106 includes an outer surface 125 that includes one or more threads 127 adjacent the open end 117. The threads 121 of the second portion 104 are configured to cooperate and engage with the threads 127 of the third portion 106, such that the second portion 104 and the third portion 106 can be coupled together. In some embodiments, the second portion 104 and the third portion 106 can be coupled together to form a second container 110 that is sealed from ambience (e.g., such that the second container 110 includes a liquid-tight seal, a hermetic seal, or a combination thereof). For example, in some embodiments, one or both of the third portion 106 and the second portion 104 can include one or more seals (e.g., o-rings).

By way of example only, the third portion 106 includes a tapered closed end 115. By way of further example, the third portion 106 includes a flange 131 which extends from a sidewall of the third portion 106 to the same distance as the terminus of the tapered closed end 115. The flange 131 can allow the third portion 106 to be stood on end to facilitate handling, storage and/or transportation of the third portion 106.

The first portion 102, the second portion 104, and the third portion 106 can be formed of a variety of materials, including, but not limited to, polymeric materials, metals (e.g., aluminum, stainless steel, etc.), ceramics, glasses, and combinations thereof. Examples of polymeric materials can include, but are not limited to, polyolefins (e.g., polyethylene, polypropylene, combinations thereof, etc.), polycarbonate, acrylics, polystyrene, high density polyethylene (HDPE), polypropylene, other suitable polymeric materials capable of forming a freestanding and/or self-supporting container, or a combination thereof. The first portion 102, the second portion 104, and the third portion 106 can be translucent (or even transparent), or opaque, and can be any suitable size, depending on the type, amount and/or size of sample to be concentrated, and the type, amount and/or size of concentrate to be collected. For example, in some embodiments, the first portion 102 can have a capacity of at least about 1 mL, at least about 5 mL, at least about 10 mL, at least about 25 mL, at least about 50 mL, at least about 100 mL, or at least about 250 mL. In some embodiments, the second portion 104 can have a capacity of no greater than about 1 mL, no greater than about 2 mL, no greater than about 5 mL, or no greater than about 10 mL. In some embodiments, the third portion 106 can have a capacity of no greater than about 1 mL, no greater than about 5 mL, or greater than about 10 mL.

The shapes, dimensions and coupling means for the first portion 102 and the second portion 104 are described above and illustrated in FIG. 1 by way of example only. It should be understood, however, that a variety of shapes and dimensions of the first portion 102 and the second portion 104 can be used. In addition, a variety of coupling means can be employed to removably couple the first portion 102 and the second portion 104, including, but not limited to, a clamp (e.g., a spring-loaded clamp, a snap-type clamp, etc.); a clip (e.g., a spring-loaded clip, etc.); ties (e.g., wire ties); one or more magnets; tape; an adhesive; a cohesive; a hook-and-loop fastener; snap-fit engagement (e.g., wherein the second portion 104 functions as a flip-top cap); press-fit engagement (also sometimes referred to as "friction-fit engagement" or "interference-fit engagement"); thermal bonding (e.g., heat and/or pressure applied to one or both of the components to be coupled); other suitable coupling means; and combinations thereof.

In some embodiments, as shown in FIG. 1, the first portion 102 and the third portion 106 can include indicia 132 and 134, respectively, which can be used to facilitate adding a desired volume to the first portion 102 and/or third portion 106.

In some embodiments, the second portion 104 can include one or more recesses 136 adapted to retain a concentrate of the sample to be concentrated, each recess 136 opening toward the open end 118 of the second portion 104. Each recess 136 can include at least one of a well, a depression, a channel, and the like, and combinations thereof. In some embodiments, the one or more recesses 136 can include the channels or interstitial spaces between outwardly-projecting microstructures, such as those described in Ylitalo et al., U.S. Pat. No. 6,386,699. In some embodiments, one or more of the recesses 136 can include a surface modification (e.g., such as a hydrophilic/oleophilic surface treatment or coating) to facilitate retaining a concentrate of interest. The recesses 136 need not all be the same shape or size, and in some embodiments, the second portion 104 includes a variety of recesses 136, ranging from microstructured to larger, and having a variety of shapes and configurations. In some embodiments, the one or more recesses 136 can be formed directly into the inner surface 120 of the second portion 104, and in some embodiments, the one or more recesses 136 can be formed in a substrate that is coupled to the inner surface 120 of the second portion 104.

In some embodiments, as will be described in greater detail with respect to FIG. 3, at least a portion of the inner surface 120 of the second portion 104 can include a microstructured surface 138. In embodiments employing the microstructured surface 138, the one or more recesses 136 can be microstructured recesses 136, and the microstructured surface 138 can include a variety of microstructured features.

In some embodiments, the volume of the first portion 102 (i.e., the capacity of the first portion 102) is at least about 1 mL, in some embodiments, at least about 10 mL, and in some embodiments, at least about 100 mL. In some embodiments, the volume of the first portion 102 ranges from about 1 mL to about 100 mL. As a result, in some embodiments, the volume of the sample is at least about 1 mL, in some embodiments, at least about 10 mL, and in some embodiments, at least about 100 mL. In some embodiments, the volume of the sample is no greater than about 200 mL, in some embodiments, no greater than about 100 mL, in some embodiments, no greater than about 75 mL, and in some embodiments, no greater than about 50 mL. In some embodiments, the volume of the sample ranges from about 1 mL to about 100 mL.

In some embodiments, the second portion 104 includes a volume and/or the one or more recesses 136 include a collective volume of (i.e., a capacity to retain a volume of concentrate 154 of) at least about 1 microliter (μL), in some embodiments, at least about 5 μL, in some embodiments, at least about 10 μL, and in some embodiments, at least about 25 μL. In some embodiments, the second portion 104 includes a volume and/or the one or more recesses 136 include a collective volume of no greater than 200 μL, in some embodiments, no greater than about 100 μL, in some embodiments, no greater than about 75 μL, and in some embodiments, no greater than about 50 μL. In some embodiments, the volume of the second portion 104 and/or the collective volume of the one or more recesses 136 ranges from about 1 μL to about 100 μL.

In some embodiments, the ratio of the volume of the first portion 102 to the volume of the second portion 104 is at least about 10:1, in some embodiments, at least about 100:1 ($10^2$:1), in some embodiments, at least about 1000:1 ($10^3$:1), in some embodiments, at least about 10,000:1 ($10^4$:1), and in some embodiments, at least about 100,000:1 ($10^5$:1). In some embodiments, the ratio of the volume of the first portion 102 to the volume of the second portion 104 ranges from about 10:1 to about $10^5$:1.

In some embodiments, the concentration increase (i.e., the concentration (e.g., of the more dense matter, such as the analyte(s) of interest) of the resulting concentrate retained in the second portion 104, divided by the concentration of the initial sample, expressed as a ratio) can be at least about 10:1, in some embodiments, at least about 100:1 ($10^2$:1), in some embodiments, at least about 1000:1 ($10^3$:1), in some embodiments, at least about 10,000:1 ($10^4$:1), and in some embodiments, at least about 100,000:1 ($10^5$:1). In some embodiments, the concentration efficiency ranges from about 10:1 to about $10^5$:1.

With reference to FIGS. 2A-2E, a sample concentration method 150 will now be described, with continued reference to the sample concentration system 100 of FIG. 1, with the flange 130 of the first portion 102 and the flange 131 of the third portion 106 removed for simplicity and clarity.

As shown in FIG. 2A, a sample 152 can be positioned in the first container 108 formed of the first portion 102 and the second portion 104, and the first container 108 can be inverted and centrifuged in a first direction (or orientation) $D_1$ toward the second portion 104. Such a centrifugation process can cause a concentrate 154 (see FIG. 3) comprising the more dense matter of the sample 152 to be moved into the second portion 104, and particularly, into the one or more recesses 136 formed in the second portion 104.

In the first centrifugation step shown in FIG. 2A, the centrifugation g-force and/or duration necessary to form and retain the concentrate 154 in the second portion 104 can vary depending on one or more of the composition of the sample 152 to be concentrated, the analyte(s) of interest, and the like. In some embodiments, the amount of g-force required to concentrate the analyte(s) of interest can depend on the size and density of the analyte, the density and viscosity of the diluent, and the volume of sample 152 in the first portion 102 (i.e. the height of the sample 152 in the first portion 102 defines the distance the analyte needs to migrate under a specified g-force to reach the second portion 104). The sedimentation velocity (V, in centimeters per second (cm/s)) can be approximated using the formula:

$$V = 2ga^2(\rho 1 - \rho 2)/9\eta$$

where g=acceleration in cm/s² (i.e., g-force in gs*980 cm/s²), $\rho 1$=analyte density in g/cm³, $\rho 2$=density of sample media (e.g., diluent) in g/cm³, $\eta$=coefficient of viscosity in poises (g/cm/s), and a=analyte radius in centimeters (assuming a spherical shape). In some centrifuges, the g-force can be determined by the rotational speed (e.g., in revolutions per minute (RPM)) and the distance of the sample from the center of the rotor (i.e. the sample experiences a higher g-force at the same rotational speed if it is placed further away from the rotor). As a result, in order to collect the analyte(s) of interest that may reside in the sample 152 furthest from the second portion 104, the distance between the center of the rotor and the height of the sample 152 positioned closest to the rotor can be calculated to estimate what the g-force would need to be to move the analyte(s) of interest the furthest distance in the sample to maximize collection of the analyte(s) of interest.

The sedimentation velocity can be calculated using the above equation, and then the centrifugation time (i.e., duration) can be calculated by dividing the distance (e.g., the maximum distance) the analyte(s) of interest, if present, would need to travel, by the sedimentation velocity. Alternatively, the desired time and distance can be used to estimate a sedimentation velocity, and the necessary g-force can then be calculated using the above equation.

In some embodiments, the g-force in the first centrifugation step can be at least about 500 g (e.g., 500*9.8 m/s$^2$ on earth, at sea level), in some embodiments, at least about 1000 g, and in some embodiments, at least about 5000 g. In some embodiments, the g-force in the first centrifugation step can be no greater than about 100,000 g, in some embodiments, no greater than about 50,000 g, and in some embodiments, no greater than about 10,000 g.

In some embodiments, the duration of the first centrifugation step can be at least about 1 minute, in some embodiments, at least about 5 minutes, and in some embodiments, at least about 10 minutes. In some embodiments, the duration of the first centrifugation step can be no greater than about 120 minutes, in some embodiments, no greater than about 60 minutes, and in some embodiments, no greater than about 20 minutes.

As shown in FIG. 2B, the first container 108 can then be inverted, such that a supernatant 156 resulting from the first centrifugation step is decanted from the second portion 104, while the concentrate 154 remains retained in the second portion 104. The term "inverted" is used herein to refer to a change in orientation and can include orienting at a variety of angles, and is not limited to changing the orientation by 180 degrees. The second portion 104 can be adapted to retain the concentrate 154 under normal gravitational forces (e.g., under standard gravity, i.e., the standard value of Earth's gravitational acceleration at sea level, 9.8 m/s$^2$). That is, the concentrate 154 can be retained in the second portion 104 until a sufficient g-force is applied (e.g., in a second direction $D_2$, as shown in FIG. 2D) to remove the concentrate 154 form the second portion 104, irrespective of the orientation of the second portion 104.

The second portion 104 can then be removed from the first portion 102, as shown in FIG. 2C. In some embodiments, the first portion 102, comprising the supernatant 156, can be used in subsequent processing steps (e.g., repeated centrifugation steps, such as the centrifugation step illustrated in FIG. 2A), and in some embodiments, the first portion 102 and the supernatant 156 can be discarded.

FIG. 3 illustrates a cross-sectional view of the second portion 104 in FIG. 2C, with the concentrate 154 retained in the recesses 136 of the second portion 104. As shown in FIG. 3, the one or more recesses 136 (e.g., microstructured recesses 136 forming a microstructured surface 138) can be formed in the inner surface 120 of the second portion 104. In some embodiments, as shown in FIG. 3, the concentrate 154 can include insoluble matter 158 and a liquid 160, which can also include soluble matter, and particularly, soluble matter having a lower density than the insoluble matter 158. The concentrate 154, and particularly, the insoluble matter 158 (if present) can include the analyte(s) of interest (e.g., the microorganism(s) of interest), if present in the sample 152.

As shown in FIG. 2D, the second portion 104 comprising the concentrate 154 can then be coupled to the third portion 106 to form the second container 110. The second container 110 can then be centrifuged in a second direction (or orientation) $D_2$ away from the second portion 104. Such a centrifugation process can cause the concentrate 154 comprising the analyte(s) of interest (if present) to be removed from the one or more recesses 136 in the second portion 104, and moved into the third portion 106, and particularly, into the tapered closed end 115 of the third portion 106. In some embodiments, the concentrate 154 can form a pellet 162 at the bottom of the third portion 106, as shown in FIG. 2E. The concentrate 154 can then be further processed, for example, to elucidate the presence, quantity, and/or viability of the analyte(s) of interest.

In the second centrifugation step shown in FIG. 2D, the centrifugation g-force, duration and/or number of cycles necessary to remove the concentrate 154 from the one or more recesses 136 of the second portion 104 can vary depending on one or more of the composition of the concentrate 154, the analyte(s) of interest, the shape, dimensions and surface energy of the recesses 136, the surface energy of the concentrate 154 (e.g., the surface energy of any diluent present in the concentrate 154), and the like.

In some embodiments, the g-force in the second centrifugation step can be at least about 500 g, in some embodiments, at least about 1000 g, and in some embodiments, at least about 5000 g. In some embodiments, the g-force in the second centrifugation step can be no greater than about 100,000 g, in some embodiments, no greater than about 50,000 g, and in some embodiments, no greater than about 10,000 g.

In some embodiments, the duration of the second centrifugation step can be at least about 10 seconds, in some embodiments, at least about 1 minutes, and in some embodiments, at least about 5 minutes. In some embodiments, the duration of the second centrifugation step can be no greater than about 60 minutes, in some embodiments, no greater than about 30 minutes, and in some embodiments, no greater than about 10 minutes.

The sample concentration method 150 illustrated in FIGS. 2A-2E and described above can provide efficient collection of the concentrate 154 of the sample 152 (i.e., and any analyte(s) of interest that may be present in the sample 152) with minimal loss of the sample 152 and/or the concentrate 154. For example, efficient collection can be achieved by essentially "trapping" the concentrate 154 (comprising the analyte(s) of interest, if present) in the second portion 104 during the first centrifugation step illustrated in FIG. 2A. The sample concentration method 150 can further provide small-volume elution of the concentrate 154, the concentrate 154 having a much higher concentration than the sample 152 of any analyte(s) of interest that may have been present in the sample 152. For example, elution of a small, concentrated final volume can be achieved by the second centrifugation step illustrated in FIGS. 2D and 2E, where the concentrate 154 is removed from the second portion 104 and moved into the third portion 106.

Based on the centrifugation parameters employed in the centrifugation steps, and/or on the number, shape and dimensions of the recesses 136 employed in the second portion 104, the mass and/or volume of the concentrate 154 retained in the second portion 104 can be determined. That is, the second portion 104 (and/or the centrifugation steps) can be configured according to the sample 152 to be concentrated and the desired analyte(s) of interest. In some embodiments, the second portion 104 can be used to obtain a predictable volume each time, because the volume of the recesses 136 of the second portion 104 are constant. In some embodiments, a more concentrated initial sample 152 can be added to the first container 108, and the constant volume/size of the recesses 136 of the second portion 104 can be used to obtain a known number or amount of one or more analytes of interest, for example, a known cell population of a given microorganism of interest. The recesses 136 of the second portion 104 will be now described in greater detail.

Returning to FIG. 3, the one or more recesses 136 can be formed in the inner surface 120 of the second portion 104 and/or the one or more recesses 136 can be formed in a substrate that can be coupled to the inner surface 120 of the second portion 104. In embodiments employing a substrate, the thickness of the substrate can be at least about 25 micrometers, in some embodiments, at least about 100 micrometers, and in some embodiments, at least about 400 micrometers. In some embodiments, the thickness of the substrate can be no greater than about 2000 micrometers, in some embodiments, no greater than about 1000 micrometers, and in some embodiments, no greater than about 250 micrometers.

FIG. 3 illustrates the recesses 136 according to one embodiment of the present disclosure. In the embodiment illustrated in FIGS. 1 and 2, the recesses 136, which can be wells and/or channels) are defined at least partially by a plurality of walls 142. In embodiments in which the recesses 136 include wells, the plurality of walls 142 can include a plurality of intersecting walls 142.

In some embodiments, the one or more recesses 136 are microstructured recesses 136 and define the microstructured surface 138. In such embodiments, the microstructured surface 138 can be formed by a variety of methods, including a variety of microreplication methods, including, but not limited to, casting, coating, and/or compressing techniques. For example, microstructuring of the microstructured surface 138 can be achieved by at least one of (1) casting a molten thermoplastic using a tool having a microstructured pattern, (2) coating of a fluid onto a tool having a microstructured pattern, solidifying the fluid, and removing the resulting film, and/or (3) passing a thermoplastic film through a nip roll to compress against a tool having a microstructured pattern (i.e., embossing). The tool can be formed using any of a number of techniques known to those skilled in the art, selected depending in part upon the tool material and features of the desired topography. Illustrative techniques include etching (e.g., chemical etching, mechanical etching, or other ablative means such as laser ablation or reactive ion etching, etc., and combinations thereof), photolithography, stereolithography, micromachining, knurling (e.g., cutting knurling or acid enhanced knurling), scoring, cutting, etc., or combinations thereof.

Alternative methods of forming the microstructured surface 138 include thermoplastic extrusion, curable fluid coating methods, and embossing thermoplastic layers, which can also be cured. Additional information regarding the substrate material and various processes for forming the microstructured surface 138 can be found, for example, in Halverson et al., PCT Publication No. WO 2007/070310 and US Publication No. US 2007/0134784; Hanschen et al., US Publication No. US 2003/235677; Graham et al., PCT Publication No. WO2004/000569; Ylitalo et al., U.S. Pat. No. 6,386,699; and Johnston et al., US Publication No. US 2002/0128578 and U.S. Pat. Nos. 6,420,622, 6,867,342, and 7,223,364, all of which are incorporated herein by reference.

With microreplication, the microstructured surface 138 can be mass produced without substantial variation from product-to-product and without using relatively complicated processing techniques. In some embodiments, microreplication can produce a microstructured surface that retains an individual feature fidelity during and after manufacture, from product-to-product, that varies by no more than about 50 micrometers. In some embodiments, the microstructured surface 138 retains an individual feature fidelity during and after manufacture, from product-to-product, which varies by no more than 25 micrometers. In some embodiments, the microstructured surface 138 comprises a topography (i.e., the surface features of an object, place or region thereof) that has an individual feature fidelity that is maintained with a resolution of between about 50 micrometers and 0.05 micrometers, and in some embodiments, between about 25 micrometers and 1 micrometer.

The recesses 136 are adapted to retain the concentrate 154 resulting from the first centrifugation step illustrated in FIG. 2A and described above. Each recess 136 is shown in FIG. 3 as having a generally rectangular cross-sectional shape and as being formed by at least two walls 142 and a base 146, and each recess 136 is separated from an adjacent recess 136 by a wall 142. However, it should be understood that the recesses 136 can include a variety of shapes, as long as the recesses 136 are defined in the inner surface 120 of the second portion 104 and/or a substrate adapted to be coupled to the inner surface 120, so as to be able to retain the concentrate 154. Said another way, each recess 136 can be shaped and dimensioned to provide a reservoir for the concentrate 154.

Figure 4:
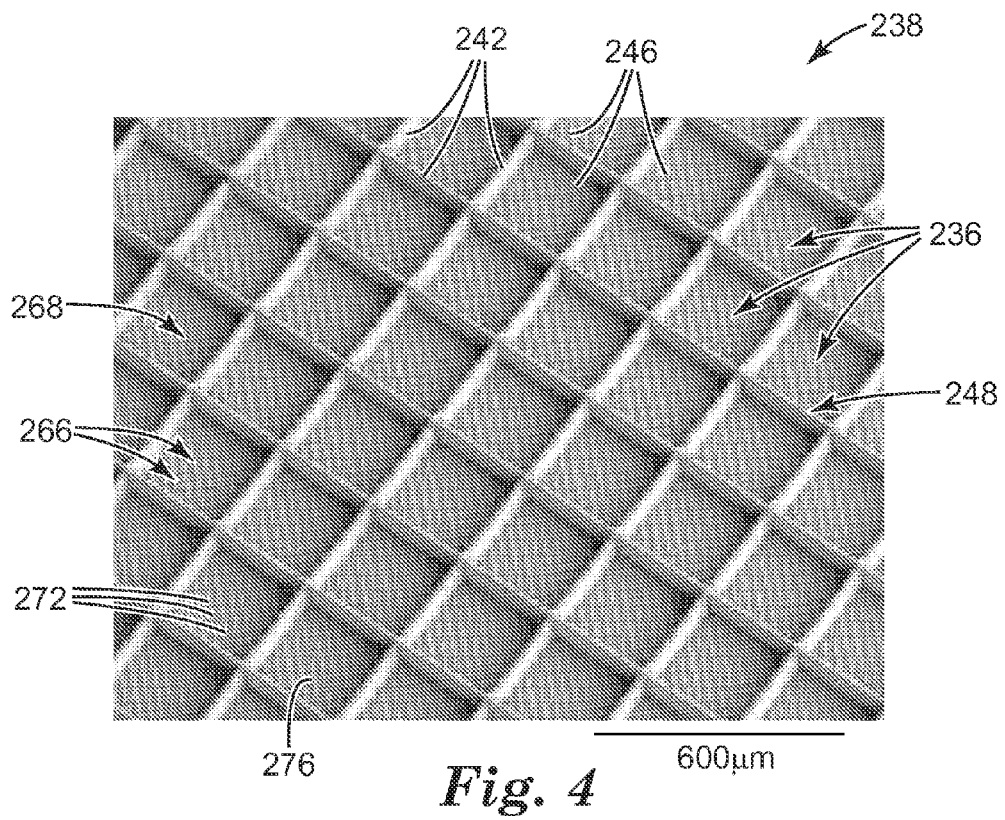
FIG. 4 is an optical micrograph of a microstructured surface according to one embodiment of the present disclosure.
Figure 5:
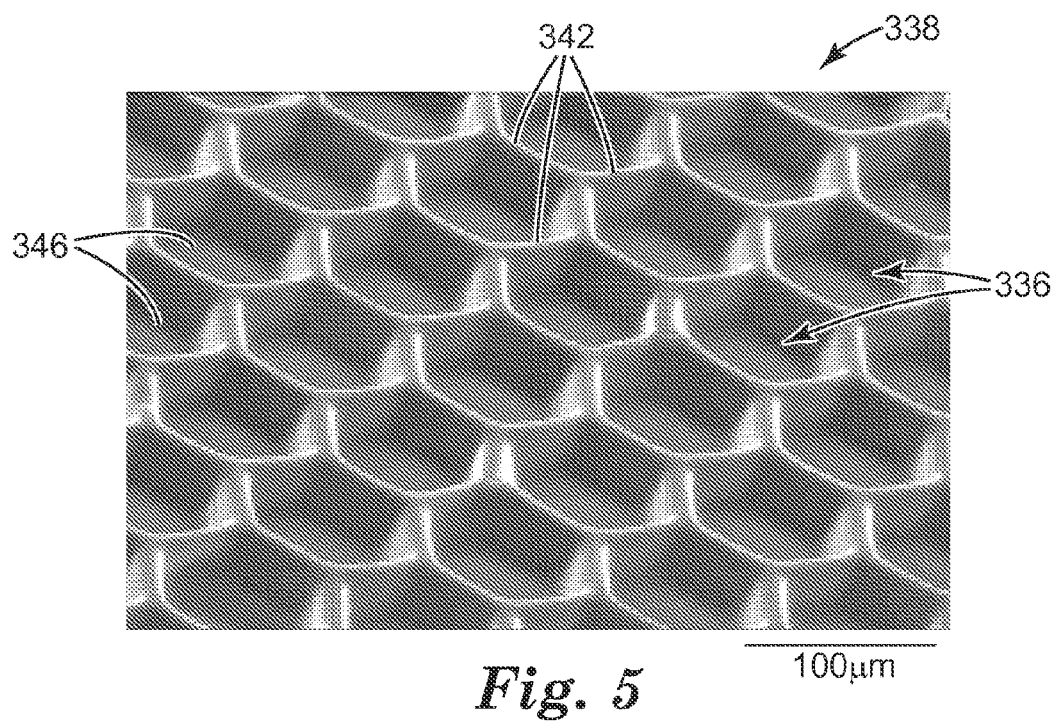
FIG. 5 is an optical micrograph of a microstructured surface according to another embodiment of the present disclosure.

Whether the recesses 136 include wells, depression, channels or a combination thereof, examples of suitable recess shapes can include, but are not limited to, a variety of polyhedral shapes, parallelepipeds (e.g., as shown in FIGS. 3 and 4), prismatoids, prismoids, etc., and combinations thereof. For example, the recesses 136 can be polyhedral, conical, frusto-conical, pyramidal, frusto-pyramidal, spherical, partially spherical, hemispherical, ellipsoidal, dome-shaped, cylindrical, cube-corner shaped (e.g., see FIG. 6, which illustrates a tool (mold) used to form a pyramidal or cube-corner microstructured surface used in the Examples), etc., and combinations thereof. Furthermore, the recesses 136 can have a variety of cross-sectional shapes (including a vertical cross-section as shown in FIG. 3, a horizontal cross-section, or a combination thereof), including, but not limited to, at least one of parallelograms, parallelograms with rounded corners, rectangles, squares, circles, half-circles, ellipses, half-ellipses, triangles, trapezoids, stars, other polygons (e.g., hexagons, as shown in FIG. 5 below), etc., and combinations thereof.

In some embodiments, the recesses 136 are shaped to include edges or corners. Such edges or corners can facilitate the retention of the concentrate 154 in the recesses 136 and can inhibit the concentrate 154 from being removed from the recesses 136 under normal gravitational forces. For example, in embodiments in which the concentrate 154 has a high surface energy, or in which the concentrate 154 includes molecules that are attracted to those of the material making up the inner surface 120 of the second portion 104 or the substrate in which the recesses 136 are formed, the concentrate 154 can be preferentially attracted to edges and/or corners of the recesses 136 (i.e., where the concentrate 154 can remain in contact with two or more surfaces), rather than smooth single surfaces.

In the embodiment illustrated in FIG. 3, the base 146 of each recess 136 is flat and planar (i.e., has an area), and is substantially parallel to a major surface 148 (e.g., of the inner surface 120 of the second portion 104 and/or of a substrate adapted to be coupled to the inner surface 120). However, because other shapes of recesses 136 are possible, the base 146 need not be planar, but rather can include a point or a line that is spaced the greatest distance from the major surface 148. For example, in embodiments employing one or more hemispherical recesses 136, the base 146 of such recesses 136 can include the point in the hemisphere that is spaced the greatest distance from the major surface 148. In addition, even in embodiments employing a planar base 146, the base 146 need not be entirely flat, but rather can be at least partially curved, flat, or a combination thereof. Furthermore, even in embodiments employing a flat, planar base 146, the base 146 need not be parallel to the major surface 148, but rather can be oriented at an angle (e.g., a non-zero angle) with respect to the major surface 148.

Furthermore, in the embodiment illustrated in FIG. 3, the recesses 136 are each shown as having various lines of symmetry, and the base 146 is centered with respect to the opening of the recess 136. However, it should be understood that the recesses 136 need not include any lines of symmetry, and the base 146 (whether the base 146 includes a point, a line or an area) need not be centered with respect to the opening of the recess 136.

The recesses 136 illustrated in FIG. 3 are shown by way of example only as being of the same size and shape; however, it should be understood that all of the recesses 136 do not need to be of the same size or shape. That is, the recesses 136 can all be formed of about the same shape and size, the same or similar shape but different sizes, different shapes but similar sizes, different shapes and sizes, or a combination thereof. For example, in some embodiments, the recesses 136 can include a pattern of alternating sizes of similarly-shaped recesses 136, or regions of recesses 136 wherein the recesses 136 of one region are of the same size (or shape) but are not of the same size (or shape) as an adjacent region, and the like, and combinations thereof.

Furthermore, the recesses 136 illustrated in FIG. 3 are shown by way of example only as being regularly arranged (e.g., in a cellular array in embodiments in which the recesses 136 include wells). However, it should be understood that the recesses 136 can include a variety of regular arrangements or arrays, random arrangements, or combinations thereof. In some embodiments, the recesses 136 are arranged randomly on a local or smaller scale, but the random arrangements repeat, or are ordered, on a larger scale. Alternatively, in some embodiments, the recesses 136 are ordered on a smaller scale, but the ordered regions are randomly arranged on a larger scale.

In addition, in the embodiment illustrated in FIG. 3, the walls 142 are all of the same size and shape. However, it should be understood that a variety of other wall shapes are possible. For example, the walls 142 need not include a substantially rectangular cross-sectional shape, but rather can include any of the above-described cross-sectional shapes.

The walls 142 and the recesses 136 can be characterized by a variety of sizes, dimensions, distances between walls 142 or recesses 136, relative sizes, etc. The walls 142 generally have dimensions such as thickness, height, length, width, etc. The recesses 136 generally have volumes with dimensions such as a radius, diameter, height, width, length, etc. Generally, the walls 142 and/or the recesses 136 are sized, shaped and spaced to retain the concentrate 154 in the recesses 136 when second portion 104 is in any orientation (e.g., by capillary forces).

In some embodiments, the walls 142 can have an average thickness of at least about 1 micrometer, in some embodiments, at least about 5 micrometers, and in some embodiments, at least about 10 micrometers. In some embodiments, the walls 142 can have an average thickness of no greater than about 50 micrometers, in some embodiments, no greater than about 30 micrometers, and in some embodiments, no greater than about 20 micrometers.

In some embodiments, the walls 142 can be shaped and/or sized to minimize the area of the top surface of the walls 142 so that any matter collected on the top surface of the walls 142 can be diverted into an adjacent recess 136. For example, in some embodiments, the walls 142 can include a taper toward the top surface. In some embodiments, the top surface can include a convex shape. In some embodiments, a combination of a taper and a convex shape can be employed.

In some embodiments, the configuration of the walls 142 and the recesses 136 in any given region can be chosen such that the average wall or recess pitch (i.e., the center to center distance between adjacent walls 142 or recesses 136, respectively) is at least about 1 micrometer, in some embodiments, at least about 10 micrometers, and in some embodiments, at least about 50 micrometers. In some embodiments, the average wall or recess pitch is no greater than about 1000 micrometers, in some embodiments, no greater than about 500 micrometers, and in some embodiments, no greater than about 400 micrometers.

In some embodiments, the recesses 136 can be characterized by an x-direction dimension in the plane of the major surface 148 (e.g., a length, a width, a radius, a diameter, a diagonal, etc.). The phrase "in the plane of" is used to generally refer to an x-y plane dimension, and is only used to distinguish from a depth or a z-direction dimension, but does not require the dimension to be located exactly in the plane of the major surface 148, but rather can include dimensions that lie in other similar x-y planes that are substantially parallel to the plane of the major surface 148. In some embodiments, the average recess x-direction dimension (e.g., the width of the base 146) is at least about 1 micrometer, in some embodiments, at least about 10 micrometers, and in some embodiments, at least about 50 micrometers. In some embodiments, the average recess x-direction dimension is less than about 1000 micrometers, in some embodiments, less than about 500 micrometers, and in some embodiments, less than about 100 micrometers.

In some embodiments, the average recess volume is at least about 1 picoliter (pL), in some embodiments, at least about 10 pL, in some embodiments, at least about 100 pL, and in some embodiments, at least about 1000 pL (1 nL). In some embodiments, the average recess volume is no greater than about 1,000,000 pL (1 µL), in some embodiments, no greater than about 100,000 pL, and in some embodiments, no greater than about 10,000 pL.

Another way to characterize the walls 142 and the recesses 136 is to describe them in terms of their aspect ratios. An "aspect ratio" of a recess 136 is the ratio of the depth of a recess 136 to the width of the recess 136. An "aspect ratio" of a wall 142 is the ratio of the height of the wall 142 to the width (or thickness) of the wall 142. In some embodiments, the average recess aspect ratio is at least about 0.01, in some embodiments, at least about 0.05, and in some embodiments, at least about 1. In some embodiments, the average recess aspect ratio is no greater than about 2, in some embodiments, no greater than about 1, and in some embodiments, no greater than about 0.8.

In some embodiments, the average wall aspect ratio is at least about 0.01, in some embodiments, at least about 0.05, and in some embodiments, at least about 1. In some embodiments, the average wall aspect ratio is no greater than about 15, in some embodiments, no greater than about 10, and in some embodiments, no greater than about 8.

In some embodiments, the average height of the walls 142 or the average depth of the recesses 136 (i.e., the distance between the base 146 of the recess 136 and the top of the recess 136, i.e., the adjacent portion of the major surface 148)

is at least about 5 micrometers, in some embodiments, at least about 20 micrometers, and in some embodiments, at least about 30 micrometers. In some embodiments, the average height of the walls 142 or the average depth of the recesses 136 can be no greater than about 200 micrometers, in some embodiments, no greater than about 100 micrometers, and in some embodiments, no greater than about 50 micrometers. In the embodiment illustrated in FIG. 3, the wall height is substantially the same as the recess depth; however, it should be understood that this need not be the case. For example, in some embodiments, the recesses 136 include a portion that is recessed even below the bottom of the walls 142, such that the well depth is greater than the wall height. However, even in such embodiments, the above size ranges can apply.

Whether or not the recesses 136 or the walls 142 are themselves microstructured, the second portion 104 can include a microstructured surface 138 that includes additional microstructured features, such as protrusions, depressions or recesses, or a combination thereof. At least some of the microstructured features can be formed on a nano-, micro- or macro-scale. Each microstructured feature can be defined by two or more dimensions (e.g., one or more dimensions into/out of the plane of the major surface 148 and one or more dimensions in the plane of the major surface 148). In some embodiments, the major surface 148 includes a configuration of microstructured features, such that at least two dimensions of each of the features are microscopic. The "features" can include any of the above-described microstructured features formed in the major surface 148, including the walls 142, the recesses 136, or any other microstructured features formed on the major surface 148. "Microscopic features" are sufficiently small so as to require an optic aid to the naked eye to determine their shape. In some embodiments, the dimensions of the microstructured features can be no greater than 200 micrometers in at least two of the possible dimensions.

The microstructured features can have a desired characteristic size (e.g., length, width, depth, radius, diameter, or other dimension measured along any direction) and density (e.g., features per unit area of the major surface 148). A feature can be configured such that its characteristic length in all three directions (e.g., x, y (in the plane of the major surface 148) and z (into/out of the plane of the major surface 148)) is similar. Alternatively, a feature can be configured such that the characteristic length in one or more directions is greater than in the other directions.

In some embodiments, a feature can have a maximum characteristic length in one or more dimensions of no greater than about 500 micrometers. In some embodiments, the maximum characteristic length is 50 micrometers, and in some embodiments, the characteristic maximum length is 10 micrometers. In some embodiments, the minimum characteristic length in one or more dimensions is 1 nanometer. In some embodiments, the minimum characteristic length is 10 nanometers, and in some embodiments, the minimum characteristic length is 100 nanometers. Furthermore, in some embodiments, the feature density is at least 100 features per square millimeter ($mm^2$), in some embodiments, at least 1,000 features per $mm^2$, and in some embodiments, at least 10,000 features per $mm^2$.

FIG. 4 illustrates a microstructured surface 238 according to another embodiment of the present disclosure, employing primary and secondary microstructured features. The microstructured surface 238 shares many of the same elements and features described above with reference to the illustrated embodiment of FIG. 3. Accordingly, elements and features corresponding to the elements and features of the illustrated embodiment of FIG. 3 are provided with the same reference numerals in the 200 series. Reference is made to the description above accompanying FIG. 3 for a more complete description of the features and elements (and alternatives to such features and elements) of the embodiment illustrated in FIG. 4.

The microstructured surface 238 includes major surface 248 defined at least partially by a plurality of primary intersecting walls 242, and particularly, by an upper surface of the plurality of primary intersecting walls 242. The major surface 248 can also be referred to as the "primary microstructured surface" 248. The primary microstructured surface 248 includes a plurality of primary recesses 276 (i.e., which are defined as wells in FIG. 4) that are each defined at least partially by four primary walls 242 and a primary base 246.

The microstructured surface 238 further includes a second level or degree of microstructures. Particularly, the microstructured surface 238 includes a secondary major surface 268, which can also be referred to as a "secondary microstructured surface" 268. The secondary microstructured surface 268 is defined at least partially by a plurality of secondary intersecting walls 272, and particularly, by an upper surface of the plurality of secondary intersecting walls 272. In the embodiment illustrated in FIG. 4, the upper surfaces of the plurality of secondary walls 272 are spaced a distance from the major surface 248, such that the secondary walls 272 are recessed relative to the major surface 248 of the microstructured surface 238.

The secondary microstructured surface 268 is further defined by a plurality of secondary recesses 266 (i.e., which are defined as wells in FIG. 4) that are each at least partially defined by four secondary walls 272 and a secondary base 276. The secondary base 276 is spaced a distance from the primary microstructured surface 248, and is spaced a distance from the secondary microstructured surface 268. In the embodiment illustrated in FIG. 4, the primary bases 246 are each at least partially defined by the plurality of secondary bases 276, and the secondary bases 276 are positioned the same distance from the primary microstructured surface 248 as the primary bases 246. However, it should be understood that the secondary bases 276 need not be positioned at the same depth as the primary bases 246, but rather, the secondary bases 276 can be positioned an additional distance from the primary microstructured surface 248 and can be spaced a distance from the respective primary base 246 as well. For example, in some embodiments, one or more of the primary recesses 236 can include one or more secondary recesses 266 positioned such that the secondary recess(es) 266 define a stepped configuration between the primary base 246 and the secondary base 276.

A concentrate can be positioned in the microstructured recesses 236, 266 of the microstructured surface 238, and particularly, in the secondary recesses 266. That is, each primary recess 236 and each secondary recess 266 is adapted to retain the concentrate. In the embodiment illustrated in FIG. 4, the secondary walls 272 are illustrated as being shorter than the primary walls 242; however, it should be understood that the secondary walls 272 can instead be as tall as (or more similarly sized relative to) the primary walls 242. In embodiments employing shorter secondary walls 272, the concentrate can be allowed to overfill the secondary recesses 266 and still be retained in the microstructured surface 238.

The embodiment illustrated in FIG. 4 includes two levels or degrees of microstructuring by way of example only. However, additional degrees of microstructuring in can further enhance the retention of the concentrate in the microstructured surface 238. Such additional degrees of microstructuring can include additional tertiary microstructures, quaternary microstructures, and so on. Each additional level of microstructuring can go increasingly deeper into the inner surface 120 of the second portion 104 and/or the substrate in which the microstructured surface 238 is defined, the additional wells formed can have bases spaced the same distance from the primary microstructured surface 248 as the primary bases 246, or a combination thereof.

The microstructured surface 238 of FIG. 4 shows primary recesses 236, and a plurality of secondary recesses 266 in each of the primary recesses 236. However, it should be understood that a variety of regular configurations, random configurations, or combination configurations are possible. For example, in some embodiments, random primary recesses 236 can include secondary recesses 266, or every other primary recess 236 can include secondary recesses 266, or some regions of the microstructured surface 238 can include primary and secondary recesses 236 and 266, while some regions of the microstructured surface 238 include only primary recesses 236, etc.

In the embodiment illustrated in FIG. 4, the secondary walls 272 are oriented at an angle of about 45 degrees with respect to the primary walls 242. However, it should be understood that the secondary walls 272 can instead be oriented at a variety of other angles (e.g., 0 degrees, 90 degrees, etc.) with respect to the primary walls 242. In addition, the secondary recesses 266 are illustrated as having the same shape as that of the primary recesses 236; however, it should be understood that all of the alternatives described above with respect to the recesses 136 of FIG. 3 regarding shape, number, orientation, size, etc. apply to the primary recesses 236 and the secondary recesses 266 of the microstructured surface 238 of FIG. 4.

The secondary walls 272 and recesses 266 can range in size and can be defined by the size ranges given above with respect to the walls 142 and recesses 136 of FIG. 3. Furthermore, in some embodiments, the secondary recesses 266 can have an average depth or the secondary walls 272 can have an average height of at least about 0.1 micrometers, in some embodiments, at least about 1 micrometers, and in some embodiments, at least about 2 micrometers. In some embodiments, the secondary recesses 266 can have an average depth or the secondary walls 272 can have an average height of no greater than about 50 micrometers, in some embodiments, no greater than about 20 micrometers, in some embodiments, no greater than about 10 micrometers, and in some embodiments, no greater than about 5 micrometers.

The secondary walls 272 and recesses 266 can be further defined by their relative sizes, as compared to the primary walls 242 and recesses 236. For example, in some embodiments, the average secondary wall height or the average secondary well depth is at least about 5 micrometers less than the average primary wall height or the average primary well depth, respectively. The average primary wall height and the average primary well depth, along with the other characteristics of the primary walls 242 and recesses 236 can be assumed to be the same as those described above with respect to the walls 142 and recesses 136 of FIG. 3. Furthermore, in some embodiments, the average secondary wall height or the average secondary well depth is at least about 20 micrometers less than the average primary wall height or the average primary well depth, respectively, in some embodiments, at least about 50 micrometers less, and in some embodiments, at least about 70 micrometers less.

In some embodiments, the ratio of the average primary well volume to the average secondary well volume is at least about 5, in some embodiments, at least about 30, in some embodiments, at least about 50, and in some embodiments, at least about 150. In some embodiments, the ratio of the average primary well volume to the average secondary well volume is no greater than about 2,000,000, in some embodiments, no greater than about 1,000,000, in some embodiments, no greater than about 150,000, and in some embodiments, no greater than about 500.

FIG. 5 illustrates a microstructured surface 338 according to another embodiment of the present disclosure. The microstructured surface 338 shares many of the same elements and features described above with reference to the illustrated embodiment of FIG. 3. Accordingly, elements and features corresponding to the elements and features of the illustrated embodiment of FIG. 3 are provided with the same reference numerals in the 300 series. Reference is made to the description above accompanying FIG. 3 for a more complete description of the features and elements (and alternatives to such features and elements) of the embodiment illustrated in FIG. 5.

As shown in FIG. 5, the microstructured surface 338 includes a plurality of recesses 336 adapted to retain a concentrate of a sample, for example, after the first centrifugation step illustrated in FIG. 2A. Each recess 336 illustrated in FIG. 5 is defined at least partially by six walls 342 and a base 346. As a result, each recess 336 has a hexagonal horizontal cross-sectional shape (i.e., taken along a plane generally parallel to the base 346 of each recess 336).

The microstructured surfaces 138, 238 and 338 are shown by way of example only, but it should be understood that any combination of the microstructured surfaces 138, 238 and 338 can be employed in a sample concentration system of the present disclosure. In addition, or alternatively, any other disclosed or equivalent microstructured surface can be used in the second portion 104 to retain a concentrate of a sample of interest.

The following working examples are intended to be illustrative of the present disclosure and not limiting.

EXAMPLES

The following three microstructured surfaces were used in the examples, each of which were prepared in a substrate. After the microstructured surfaces were prepared in the respective substrates, circular sections of each substrate were die cut to a diameter of 24 mm using a hole punch. The circular sections of each substrate were then adhered to the flat inner surface (i.e., underside) of a flat centrifuge cap (i.e., a CENTRISTAR™ centrifuge cap, available from Corning, Inc., Corning, N.Y.) using silicone polyurea transfer adhesive, prepared as described in Melancon et al., U.S. Pat. No. 6,730,397, which is incorporated herein by reference. To prevent leaking during centrifugation, a one-inch internal diameter o-ring gasket having a round, 0.100-inch cross section (available as part number AS568A-120 from Grainger, Inc., Lake Forest, Ill.) was placed in the outer groove of the cap. The cap including the o-ring and substrate comprising the microstructured surface served as the "second portion" of the sample concentration system in the examples.

Microstructured Surface I

The microstructured surface 238 of FIG. 4 was used in the Examples section and referred to as "Microstructured surface I." The Microstructured surface I was prepared by casting molten polypropylene resin against a cast roll with the inverse of the desired microstructured surface. Specifically, the primary recesses 236 (which were in the form of wells) and primary walls 242 of Microstructured surface I included a pitch (i.e., a center to center spacing between adjacent primary walls 242 or recesses 236, respectively) of about 250 micrometers. The primary recesses 236 were rhomboidal in shape with a nominal depth of about 67 micrometers, and the primary walls 242 were oriented at a 45 degree angle with respect to the machine direction of the substrate. The primary wall height between the primary wall intersections was about 67 micrometers, and the primary wall height in the region of the intersections was about 75 micrometers. Microstructured surface I further included secondary walls 272 that sub-divided each of the primary recesses 236 into secondary recesses 266. The secondary walls 272 were about 4 micrometers in height, and the secondary walls 272 and the secondary recesses 266 included a pitch (i.e., a center to center distance between adjacent secondary walls 272 or recesses 236, respectively) of about 25 micrometers. The secondary walls 272 were arranged such that they were either parallel or perpendicular to the machine direction of the substrate (i.e., the secondary walls 272 were arranged at an angle of about 45 degrees with respect to the primary walls 242). Additional details of the Microstructured surface I and the method of making it are described above with respect to FIG. 4 and in Halverson et al., PCT Publication No. WO 2007/070310, which is incorporated herein by reference.

Microstructured Surface II

The microstructured surface 338 of FIG. 5 was used in the Examples section and referred to as "Microstructured surface II." The Microstructured surface II was prepared from an etched master tool by compressing 3M™ ESPE™ EXPRESS™ impression material onto the tool using a glass plate to an approximate final thickness of 1 mm. The resulting Microstructured surface II included hexagonal-shaped recesses 336, as shown in FIG. 5 and described above. The hexagonal recesses 336 included a pitch (i.e., a center to center spacing between adjacent primary walls 342 or recesses 336, respectively) of about 100 micrometers. The wall height was about 50 micrometers. The cross-section of each recess 336 was rhomboidal in shape and had a sidewall angle of approximately 10 degrees.

Microstructured Surface III

Figure 6:
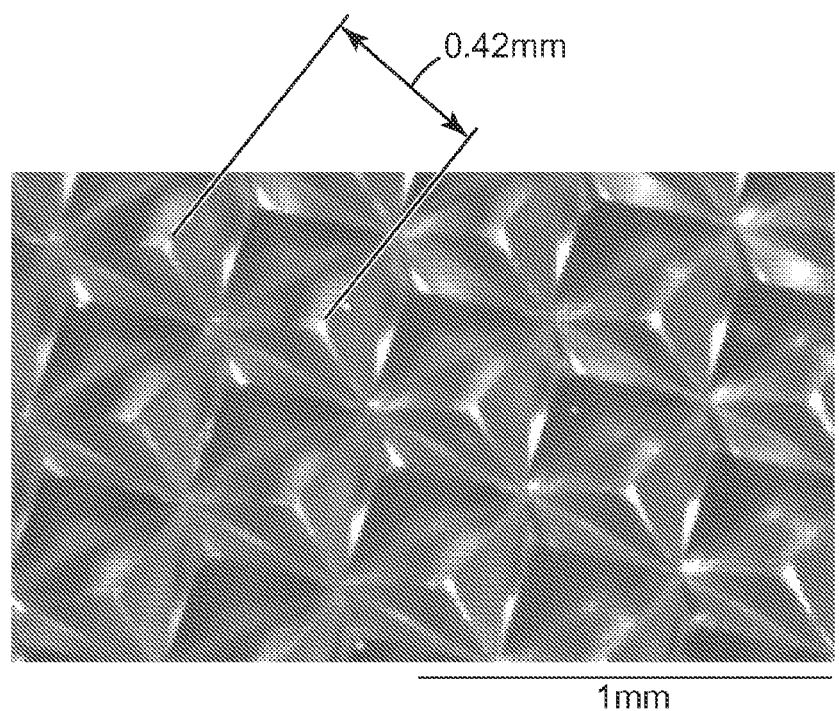
FIG. 6 is an optical micrograph of a tool used to form a microstructured surface according to one embodiment of the present disclosure and used in the Examples.

Microstructured surface III included inverted (i.e., upside down and hollow) cube-corner-shaped recesses. The Microstructured surface III was replicated from male tooling using thermally-cured polydimethylsiloxane (PDMS; available under the trade designation SYLGARD® 184 from Dow Corning Corporation, Midland, Mich.). The male tooling used was the cube-corner side of 3M™ DIAMOND GRADE™ prismatic retroreflective sheeting (available from 3M Company, St. Paul, Minn.), a scanning electron micrograph of which is shown in FIG. 6. The tooling was placed in a 100 mm×15 mm Petri dish (available as catalog number 25384-302 from VWR International, West Chester, Pa.), cube-corners pointing up. The PDMS reagents were mixed according to the manufacturer's instructions and poured onto the tooling to an approximate thickness of 1 mm. Bubbles were removed by degassing in an enclosed chamber using repeated exposures to vacuum following by exposures to atmospheric pressure. The Petri dish was covered and the PDMS was cured at 80° C. for 2 hours. After curing, the PDMS substrate was separated from the tooling, such that Microstructured surface III included pyramidal recesses.

Examples 1-3

First Centrifugation Step

The total amount of water retained in each of the three microstructured surfaces, Microstructured surface I, Microstructured surface II, and Microstructured surface III was determined gravimetrically, and reported as Example 1, Example 2, and Example 3, respectively, in Table 1. The above described "second portions" comprising centrifuge caps including one of the microstructured surfaces and an o-ring were prepared in quadruplicates. The empty second portions were weighed to obtain an initial weight. Ten milliliters of water were placed in 50-mL centrifuge tubes (available under the designation Self-Standing 50-mL centrifuge tubes, No. 430921, from available from Corning, Inc., Corning, N.Y.). The 50-mL centrifuge tubes served as the "first portion" of the sample concentration system of this example. The second portions were screwed onto the first portions to form first containers. The first containers were then place cap-down (i.e., oriented toward the second portion) in a swinging bucket centrifuge rotor (i.e., a multipurpose centrifuge available under the designation "Eppendorf Model 5804" from Eppendorf, Hamburg, Germany). The first containers were centrifuged at 3000 RPM (~1400 g) for 2 minutes to fill the microstructures and displace trapped air bubbles. The first containers were removed from the bucket and inverted. The second portions were removed from the first portions and immediately weighed to determine the mass of liquid retained by surface tension in the microstructured surfaces. Mass was converted to volume assuming a density of water to be 1 mg/µL, and the average of the quadruplicates is reported in Table 1 for each of Examples 1-3.

TABLE 1

VOLUME RETAINED ATER CENTRIFUGAL FILLING IN EXAMPLES 1-3

| MICROSTRUCTURE | TOTAL VOLUME RETAINED IN SECOND PORTION AFTER CENTRIFUGATION |
|---|---|
| Example 1 | 35 µL |
| Example 2 | 43 µL* |
| Example 3 | 37 µL* |

*including any volume trapped in the perimeter gap between the ~1 mm thick film and the cap flange. Liquid was observed in this space for thick (1 mm) films.

Examples 4-6

Second Centrifugation Step

Figure 7:
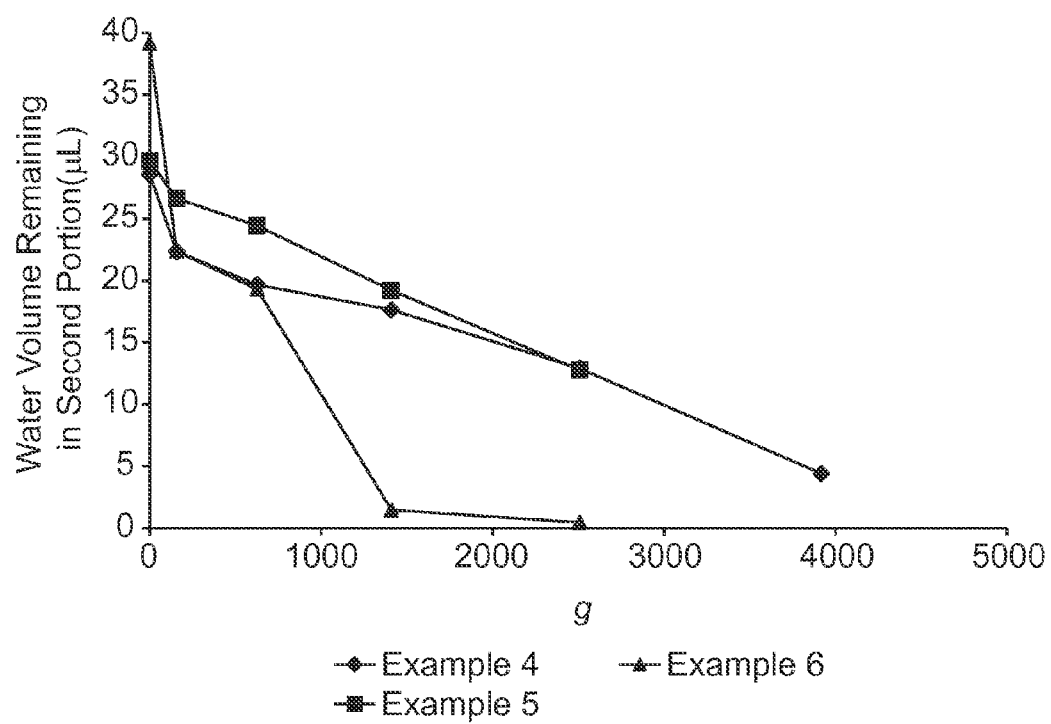
FIG. 7 is a graph of water volume vs. g-force for Examples 4-6.

The amount of gravitational force needed to expel liquid from each of Microstructured surface I, Microstructured surface II, and Microstructured surface III was determined gravimetrically, the results for which are reported as Example 4, Example 5, and Example 6, respectively in FIG. 7. The second portions were prepared and filled according to first centrifugation step described above in Examples 1-3. The second portions were removed from the first portions and coupled to fresh 50-mL centrifuge tubes (i.e., centrifuge tubes available under the designation Self-Standing 50-mL centrifuge tubes, No. 430921, from available from Corning, Inc., Corning, N.Y.) shortened to a height of 3 cm. The fresh, shortened 50-mL centrifuge tubes served as the "third portions" of Examples 4-6, and the second portions coupled to the third portions formed second containers. The second containers for each Examples 4-6 were placed in the bottom of the same centrifuge rotor that was used in Examples 1-3 (i.e., toward the third portions and away from the second portions), and centrifuged for 2 minutes at increasing gravitational forces, as reported in FIG. 7. The amount of liquid released into the third portion by the second centrifugation step was determined by weighing the second portions before and after each centrifugation at each g-force. Example 6 (comprising Microstructured surface III) appeared to release water at a lower g-force.

Examples 7-10

Bacterial Concentration

Examples 7-10 were performed using four sample concentration systems. Two of the sample concentration systems (Examples 7 and 8) included a second portion that included Microstructured surface III, prepared as described above. The other two sample concentration systems (Examples 9 and 10) included a second portion without any microstructured surfaces.

Serial dilutions of an overnight broth culture (trypticase soy broth) of E. coli were performed in Butterfield's buffer to provide a liquid sample having an approximate final concentration of 150 bacteria per mL (actual initial concentrations are recorded in Table 2. 40 mL of this liquid sample were placed in four 50-mL centrifuge tubes (available under the designation Self-Standing 50-mL centrifuge tubes, No. 430921, from available from Corning, Inc., Corning, N.Y.), which served as the "first portions" of each of Examples 7-10. For each of Examples 7-10, the second portion was coupled to a first portion to form a first container and was centrifuged at 5000 RPM (~2500 g) according to the first centrifugation step described above in Examples 1-3 (i.e., toward the second portion).

The first portions were removed from the second portions of each of Examples 7-10 after centrifugation durations of 10, 20, and 40 min. At each timepoint, each second portion was coupled to a third portion (as described in Examples 4-6) to form a second container, and the concentrate trapped in the second portion was ejected in a second centrifugation step, as described in Examples 4-6, by centrifugation at 3000 RPM (~1400 g) for 2 minutes.

Each third portion (i.e., each receiving tube) was weighed before and after the second centrifugation step at each timepoint to determine the volume of liquid collected in the third portion for each sample concentration system. The volume collected at the 20-min. timepoint for the first centrifugation step is reported for each of Examples 7-10 in Table 2.

The collected concentrate was diluted to 30 mL followed by plating 1 mL aliquots on aerobic-count 3M™ PETRI-FILM™ plates (available from 3M Company, St. Paul, Minn.) to determine the final concentration of each sample concentration system. The final concentration at the 20-min. timepoint for each of Examples 7-10 is reported in Table 2. The "Concentration Increase" for each of Examples 7-10 at the 20-min. timepoint was calculated by dividing the final concentration at the 20-min timepoint by the initial concentration for each of Examples 7-10, the results for which are reported in Table 2.

TABLE 2

BACTERIAL CONCENTRATION RESULTS FOR EXAMPLES 7-10, AFTER A 20-MINUTE FIRST CENTRIFUGATION STEP

| Sample | Volume Collected (μL) | Initial Concentration (bacteria/mL) | Final Concentration (bacteria/mL) | Concentration Increase (X) |
|---|---|---|---|---|
| Example 7 (Microstructured surface III) | 29 | 158 | 104,000 | 660 |
| Example 8 (Microstructured surface III) | 13 | 172 | 251,000 | 1,460 |
| Example 9 (no microstructured surface) | 20 (hanging drops) | 151 | 17,000 | 112 |
| Example 10 (no microstructured surface) | 29 (hanging drops) | 172 | 14,000 | 81 |

Examples 11-12

Concentration of Bacteria from a Food Source

Concentration of bacteria from a food source was demonstrated using cherry tomatoes. Two cherry tomatoes were selected to provide a total mass of ~11 grams for each of Examples 11 and 12. For each of Examples 11 and 12, the tomatoes were placed in a 3M™ Mini Paint Preparation System (product number 051131-16113, available from 3M Company, St. Paul, Minn.), followed by addition of 99 mL of Butterfield's buffer and agitated using a vortex mixer, using the systems and methods described in Halverson et al., PCT Publication No. WO 2007/137257, which is incorporated herein by reference.

A 1-mL aliquot of the suspension was plated on an aerobic-count 3M™ PETRIFILM™ plate (available from 3M Company, St. Paul, Minn.) to determine the initial bacterial concentration for each of Examples 11 and 12, which is reported in Table 4. Aliquots (30-mL) of the suspension were decanted through the filter (i.e., mesh screen) in the lid of 3M™ Mini Paint Preparation System into 50-mL centrifuge tubes (available under the designation Self-Standing 50-mL centrifuge tubes, No. 430921, from available from Corning, Inc., Corning, N.Y.), which served as the "first portions" for each of Examples 11 and 12. The second portions of Examples 11 and 12 were prepared according to Examples 7 and 8 (and included Microstructured surface III).

For each of Examples 11-12, the second portion was coupled to a first portion to form a first container and was centrifuged at 5000 RPM (~2500 g) for 20 minutes according to the first centrifugation step described above in Examples 1-3 (i.e., toward the second portion).

The bacteria were collected and enumerated as described in Examples 7-10. The volume collected is reported for each of Examples 11-12 in Table 4. The final concentration for each of Examples 11-12 is reported in Table 4. The "Concentration Increase" for each of Examples 11-12 was calculated by dividing the final concentration by the initial concentration, the results for which are reported in Table 4.

The total bacteria collected and the initial total bacteria in 30 mL were determined for each of Examples 11-12 and are reported in Table 3. In addition, the supernatant remaining in the first portion after the first centrifugation step for each of Examples 11-12 was vortexed and plated to determine the number of bacteria remaining in the supernatant of the first centrifugation step, and the results are reported in Table 3. Finally, the collection efficiency (expressed as a percentage) was calculated for each of Examples 11-12 by dividing the total bacteria collected by the initial total bacteria. The collection efficiencies are reported in Table 3.

TABLE 3

BACTERIAL COLLECTION EFFICIENCY FOR EXAMPLES 11 AND 12

| | Initial Total Bacteria in 30 mL | Total Bacteria in Supernatant after Centrifugation | Total Bacteria Collected in Microstructured surface III | Collection Efficiency (%) |
|---|---|---|---|---|
| Example 11 (Microstructured surface III) | 9600 | 1830 | 4600 | 48 |
| Example 12 (Microstructured surface III) | 9600 | 1590 | 4275 | 44 |

TABLE 4

BACTERIAL CONCENTRATION RESULTS FOR EXAMPLES 11 AND 12

| | Volume Collected (µL) | Initial Concentration (bacteria/mL) | Final Concentration (bacteria/mL) | Concentration Increase (X) |
|---|---|---|---|---|
| Example 11 (Microstructured surface III) | 26 | 320 | 177000 | 553 |
| Example 12 (Microstructured surface III) | 36 | 320 | 119000 | 371 |

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

The invention claimed is:

1. A method for concentrating a sample, the method comprising:
providing a first container adapted to contain a sample, the first container comprising a first portion and a second portion adapted to be removably coupled to the first portion, the second portion having an open end and a closed end, the closed end comprising a microstructured surface, wherein the microstructured surface comprises a plurality of recesses, each recess including a base and opening toward the open end of the second portion;
centrifuging the first container in a first orientation toward the second portion of the first container;
retaining a concentrate of the sample in the microstructured surface of the second portion of the first container;
removing the second portion of the first container from the first portion;
coupling the second portion to a third portion to form a second container; and
centrifuging the second container in a second orientation toward the third portion of the second container, such that the concentrate retained in the microstructured surface of the second portion is moved into the third portion of the second container, the second orientation being different from the first orientation.

2. The method of claim 1, wherein centrifuging the first container in the first orientation includes forming a supernatant, and further comprising removing the supernatant from the first container.

3. The method of claim 1, wherein the third portion of the second container is the first portion of the first container.

4. The method of claim 1, wherein the second orientation is oriented at an angle of 180 degrees with respect to the first orientation.

5. A system for concentrating a sample, the system comprising:
a first container adapted to contain a sample, the first container comprising a first portion and a second portion adapted to be removably coupled to the first portion, the second portion having an open end and a closed end, the closed end comprising a microstructured surface, wherein the microstructured surface comprises a plurality of recesses, each recess including a base and opening toward the open end of the second portion, the microstructure surface adapted to receive a concentrate of the sample when the first container is exposed to a first centrifugal force, the microstructured surface of the second portion further adapted to retain at least a portion of the concentrate of the sample under normal gravitational forces; and
a second container comprising the second portion and a third portion adapted to be removably coupled to the second portion, the third portion adapted to receive the concentrate from the second portion when the second container is exposed to a second centrifugal force.

6. The system of claim 5, wherein the first centrifugal force has a first direction oriented toward the second portion and the second centrifugal force has a second direction oriented toward the third portion.

7. The system of claim 6, wherein the first direction is oriented at an angle of 180 degrees with respect to the second direction.

8. The system of claim 5, wherein the plurality of recesses include at least one primary recess and at least one secondary recess.

9. The system of claim 5, wherein the average recess volume is at least 1 picoliter.

10. The system of claim 5, wherein the microstructured surface includes a collective volume of at least 1 microliter.

11. The system of claim 5, wherein the microstructured surface includes a collective volume of no greater than about 200 microliters.

12. The system of claim 5, wherein the third portion of the second container is smaller than the first portion of the first container.

13. The system of claim 5, wherein the first portion includes a first volume, wherein the second portion includes a second volume adapted to retain the concentrate, and wherein the ratio of the first volume to the second volume ranges from 10:1 to $10^5$:1.

14. The system of claim 5, wherein the first portion includes a first volume that ranges from about 1 mL to about 100 mL.

15. The system of claim 5, wherein the second portion includes a second volume adapted to retain the concentrate, the second volume ranging from about 1 microliter to about 100 microliters.

* * * * *

UNITED STATES PATENT AND TRADEMARK OFFICE
CERTIFICATE OF CORRECTION

| | | |
|---|---|---|
| PATENT NO. | : 8,535,945 B2 | Page 1 of 1 |
| APPLICATION NO. | : 13/131641 | |
| DATED | : September 17, 2013 | |
| INVENTOR(S) | : Kurt J. Halverson | |

It is certified that error appears in the above-identified patent and that said Letters Patent is hereby corrected as shown below:

In the Specification

Column 5
Line 58, Delete "Micrococaceae," and insert -- Micrococcaceae, --, therefor.

Column 24
Line 41, Delete "ATER" and insert -- WATER --, therefor.

Signed and Sealed this
Eleventh Day of March, 2014

Michelle K. Lee
*Deputy Director of the United States Patent and Trademark Office*